United States Patent [19]
Michaels

[11] 3,962,414
[45] June 8, 1976

[54] STRUCTURED BIOERODIBLE DRUG DELIVERY DEVICE

[75] Inventor: Alan S. Michaels, Atherton, Calif.

[73] Assignee: Alza Corporation, Palo Alto, Calif.

[22] Filed: Oct. 25, 1974

[21] Appl. No.: 517,982

Related U.S. Application Data

[62] Division of Ser. No. 248,168, April 27, 1972, Pat. No. 3,867,519.

[52] U.S. Cl. .................................. 424/19; 128/260; 424/14; 424/16; 424/20; 424/21; 424/22
[51] Int. Cl.² .................. A61K 9/22; A61K 9/50; A61K 9/52; A61K 9/54
[58] Field of Search ................. 128/260; 424/19–22; 252/316

[56] References Cited
UNITED STATES PATENTS

| | | | |
|---|---|---|---|
| 3,640,741 | 2/1972 | Etes | 106/170 |
| 3,755,558 | 8/1973 | Scribner | 424/47 |
| 3,773,919 | 11/1973 | Boswell et al | 424/19 |
| 3,826,258 | 7/1974 | Abraham | 128/260 |

Primary Examiner—Shep K. Rose
Attorney, Agent, or Firm—Paul L. Sabatine

[57] ABSTRACT

A drug delivery device for the continuous and controlled administration of a predetermined therapeutically effective dosage of eye drug to the eye of a mamallian patient over a prolonged period of time. The device meters the flow of polylactic acid polymer micro-encapsulated eye drug by means of a drug release rate controlling material comprised of an anionic polyvalent metal cation cross-linked polyelectrolyte. The device bioerodes in the biological environment of the patient concurrently with the dispensing or at a point in time after the dispensing of the therapeutically desired amount of drug.

9 Claims, 6 Drawing Figures

STRUCTURED BIOERODIBLE DRUG DELIVERY DEVICE

This is a division of application Ser. No. 248,168, filed Apr. 27, 1972 and now U.S. Pat. No. 3,867,519.

CROSS REFERENCE TO OTHER APPLICATION

This application is related to pending U.S. application Ser. No. 179,129 filed Sept. 9, 1971, which discloses the subject matter of this application in accord with Rule 79 of the *Rules of Practice of the U.S. Patent Office in Patent Cases*, 1970.

BACKGROUND OF THE INVENTION

1. Field of the Invention

This invention relates to a method and device for the controlled administration of drug to a patient. More particularly, this invention relates to a drug dispensing device which bioerodes in the biological environment of such patient. In preferred embodiments, the invention relates to a bioerodible device for the controlled and continuous administration of drug to a mammalian patient, especially to the eye of such patient, over a prolonged period of time. In another aspect the invention relates to a method for preparing these devices.

2. Description of the Prior Art

Many and varied compositions, products, appliances, depositors, applicators, dispensers and injectors are well known in the art in which the timing or spacing of administration or absorption of drug is regulated by the structure or physical arrangement of elements so that a single administration provides a gradual but sustained feeding of the drug to a patient by slow or differential release. The advantages of such devices are that they enable the physician to more carefully regulate the level of drug administration to the patient. A further advantage of sustained release devices is the fact that the number of times that the drug need be administered is reduced.

Where oral administration is desired, one means for obtaining the above objective is to employ capsules or tablets which release the drug at a uniform rate during the capsule's passage through the gastrointestinal tract. In the past this object has been achieved by admixing one or more inert ingredients with the drug in such a manner that these inactive materials interfere with the disintegration of the tablet or the dissolution of the drug. An obvious form of such a tablet is one wherein tablets can be composed of several alternate layers of medicament and inert material. In this manner, as each alternate protective layer disintegrates the patient receives a further dose of medicament. However, tablets of this type suffer from the disadvantage of not providing a uniform and constant drug release. Furthermore, such tablets are difficult to prepare with precision so that in many instances the desired dosage level cannot be assured. Moreover, it has not been possible to provide for prolonged release of a drug by these tablets because of their rapid rate of degradation or dissolution. Still further, degradable carriers of this type have not generally found wide acceptance because of the undesirable side effects which they often produce, for example, foreign body reaction and scar formation.

Recognizing these disadvantages, more recently there have been developed certain synthetic polymeric carriers, most notably the polysiloxane rubbers, which are designed to deliver a drug to the patient without concomitant degradation of the delivery device. Instead, the polymeric drug delivery systems are based upon the phenomenon of diffusion in which drug migrates through a polymer wall at a relatively low rate. In such a system, the drug is disposed throughout the polymeric carrier manufactured from the polymeric material.

In this regard, a significant advance has recently been made in the field of ophthalmic drug delivery systems. Thus, U.S. Pat. No. 3,416,530, granted Dec. 17. 1968 to Ness, entitled "Eyeball Medication Dispensing Tablet", and U.S. Pat. No. 3,618,604 issued Nov. 9, 1971 to Ness, entitled "Ocular Insert", disclose a drug dispensing ocular insert which releases controlled amounts of drug to the eye. These devices have the added advantage of permitting slow release of drug over prolonged periods of time. Such ocular inserts are fabricated of materials that are biologically inert, non-allergenic, and non-bioerodible in tear liquid. To initiate the therapeutic program, the ocular insert is placed in the upper or lower sac of the eye bounded by the surfaces of the sclera of the eyeball and conjunctiva of the lid. Since the material from which the ocular insert is formed is not erodible by tear liquid, it retains its integrity during the course of therapy, acting as a reservoir to continuously release drug to the eye and surrounding tissues at a controlled rate. A single such ocular insert can provide the complete ophthalmic dosage regimen for a particular time period, on the order of 24 hours or longer. More frequent repeated applications which are necessary with liquids, ointments, or water soluble lamellae are avoided. On termination of the therapeutic program the ocular insert is removed from the eye.

While the drug dispensing ocular inserts described above, which deliver precise amounts of drug to the eye continuously and in a controlled manner over a prolonged period of time, have proved to be markedly superior to the prior art ointments and liquids, there remain, however, improvements to be made. The ocular insert remains intact during the course of therapy and on termination of the therapy program must be removed, which may present difficulty and discomfort to some patients. In rare instances, the removal is made more difficult by unwanted migration of the insert to the upper fornix. Further, in ophthalmic practice physician-patient contact is often not of a sufficient degree to insure that instructions from the doctor are accurately carried out by the patient. Thus, when a non-erodible ocular insert is used, there is no certainty that the insert will be removed by the patient at the completion of treatment. This is particularly true with elderly patients who often forget or are simply unable to remove the device due to failing memory or eyesight.

Disadvantages of the same nature exist with drug delivery devices which are non-bioerodible employed in areas of the anatomy other than the eye in that at some point in time the device must be surgically or otherwise removed from the body of the patient.

OBJECTS OF THE INVENTION

Therefore, it is a primary object of this invention to provide a drug delivery device which does not suffer from the disadvantages associated with heretofore known sustained release drug delivery devices.

Another object of the invention resides in the provision of a sustained release drug delivery device which is capable of completely bioeroding within the body of the patient, re, mammals, including humans, animals, e.g., farm animals, domestic animals and the like, with no undesirable side effects.

Still another object of this invention is to provide an improved drug dispensing device for the controlled continuous and prolonged administration of drugs.

A further object of this invention is to provide an improved drug dispensing ocular insert for the controlled administration of drugs to the eye.

A still further object of this invention is to provide an improved drug dispensing ocular device for delivering drugs to the eye with increased efficacy.

Still another object of this invention is to provide an improved drug dispensing ocular device which does not have to be removed from the eye after termination of the therapeutic program.

A further object of this invention is to provide an improved drug dispensing ocular device for the controlled continuous administration of drugs to the eye over a prolonged period of time which bioerodes into innocuous products concurrently with the dispensing or at a point in time after the dispensing of the drug.

Yet another object of this invention is to provide a method for producing these improved devices.

Another object of this invention is to provide an improved method for treating a patient employing the drug delivery devices of this invention.

These objects, as well as other objects, features and advantages will become more readily apparent from the following detailed description, the drawings and the accompanying claims.

SUMMARY OF THE INVENTION

In accomplishing these objects, a primary aspect of this invention resides in a bioerodible device for the sustained administration of a therapeutically effective predetermined dosage of drug to a patient comprising one or more reservoirs each of which comprises a drug formulation confined within a polyvalent metal ion cross-linked anionic polyelectrolyte which bioerodes in the body in response to the biological environment therein by a process of polyvalent metal ion displacement.

In one preferred aspect, this invention is directed to an ocular device and resides in a bioerodible ocular insert for the controlled continuous administration of a predetermined dosage of drug to the eye. The invention shall be described in major part, by way of illustration of preferred embodiments, with application to such ocular inserts although it will be appreciated by those skilled in the art that the methods and devices described herein are not so limited in application. These latter considerations are treated hereinafter.

One embodiment of the invention resides in an ocular insert for the controlled continuous administration of a predetermined dosage of drug to the eye over a prolonged period of time, comprising a body of "bioerodible" drug release rate controlling material containing a drug formulation confined therein, the body being of an initial shape which is adapted for insertion and retention in the eye comprising a polyvalent metal ion cross-linked anionic polyelectrolyte wherein the body continuously meters the flow of a therapeutically effective amount of drug to the eye at a controlled rate over a prolonged period of time.

Another embodiment of the invention resides in an ocular insert for the controlled continuous administration of a predetermined dosage of drug to the eye, comprising (1) an inner reservoir comprised of a "biodegradable" material containing a drug formulation confined therein, and (2) an outer membrane surrounding the inner reservoir and formed from drug release rate controlling bioerodible material comprising a polyvalent metal ion cross-linked anionic polyelectrolyte which continuously meters the flow of a therapeutically effective amount of drug from the reservoir to the eye at a controlled rate over a prolonged period of time, the insert being adapted for insertion and retention in the eye.

In yet another embodiment the invention resides in a bioerodible ocular insert for the controlled continuous administration of a predetermined dosage of drug to the eye over a prolonged period of time, comprising a matrix polyelectrolyte having distributed throughout a plurality of reservoirs, each of the reservoirs comprised of a drug formulation confined within a drug release rate controlling material, the reservoirs characterized by being either;

1. a microcapsule of an initial size and configuration such as to be capable of being eliminated from the ocular cavity through the punctum with ear fluid, or
2. a microcapsule of biodegradable material;

the matrix material being permeable to the passage of drug at a higher rate than through the drug release rate controlling material, the latter material metering a therpeutically effective amount of drug from the reservoir to the eye at a controlled rate over a prolonged period of time, the insert being of an initial shape which is adapted for insertion and retention in the eye and wherein the materials comprising the insert are eliminated from the ocular cavity by bioeroding or biodegrading in the environment of the eye or the reservoir material eliminated by passage through the punctum, the eliminations taking place concurrently with the dispensing or at a point in time after the dispensing of the therapeutically desired amount of drug.

In another aspect the invention resides in a process for preparing polyvalent metal ion cross-linked anionic polyelectrolyte structures to be employed in drug delivery devices which comprises the sequential steps of:

a. forming the desired structures from a water soluble anionic polyelectrolyte,
b. contacting the structures with a solution of polyvalent metal cations to cross-link the anionic polyelectrolyte, and
c. recovering the polyvalent metal in crosslinked anionic polyelectrlyte structure.

In yet another aspect, the invention resides in another process for preparing polyvalent metal ion cross-linked anionic polyelectrolyte structures to be employed as drug release rate controlling materials which comprises the sequential steps of:

a. preparing an aqueous solution containing an initially water soluble anionic polyelectrolyte,
b. adding to the aqueous solution a polyvalent metal cation capable of reacting with the anionic polyelectrolyte to form a water insoluble cross-linked precipitate in an amount sufficient to form such a cross-linked precipitate,
c. recovering the cross-lined precipitate and adding to it water and a sufficient amount of a complexing reagent to render the precipitate water soluble by forming a coordination complex therewith,
d. forming the solution into the desired structures, and
e. removing at least substantially the complexing reagent from the solution, thereby causing the polyvalent metal cation cross-linked anionic polyelectrolyte to precipitate in the form of the desired shaped stuctures, and f. recovering the thus prepared shaped structure.

DETAILED DESCRIPTION OF THE INVENTION

In accordance with preferred embodiments of the present invention, polyvalent metal ion cross-linked anionic polyelectrolytes are employed in bioerodible ocular inserts for the controlled dispensing of predetermined dosages of drug to the eye. Polyvalent metal ion cross-lined anionic polyelectrolyte materials are hydrophilic, water insoluble in their cross-linked state, compatible with the tissues of the eye and bioerodible therein.

The term "reservoir" is used herein to define the drug-containing portion of the delivery device and is intended to connote a broad class of structures capable of fulfilling the function and, as will be hereinafter more completely developed, includes a plurality of discrete, drug-containing microcapsules or a porous, hollow, solid, gel or liquid drug-containing body of material. The microcapsule can be formed as a hollow container having the drug therein or be formed as a solid or porous particle having the drug distributed therethrough.

The term "water soluble" is defined to mean materials which are soluble in water to a degree which exceeds approximately 50 parts per million.

The term "biodegradable" or "diodegrade", as used in this specification and claims, is defined as the property or characteristic of a body of a microporous, solid or gel material to innocuously disintegrate or break down as a unit structure or entity, over a prolonged period of time, in response to the biological environment in the patient by one or more physical or chemical degradative processes, for example by enzymatic action, oxidation or reduction, hydrolysis (proteolysis), displacement, e.g., ion exchange, or dissolution by solubilization, emulsion or micelle formation, and which material is thereafter absorbed by the body and surrounding tissues, or otherwise dissipated thereby.

The term "patient" or "mammal" as used herein denotes any prospective situs for the delivery device of this invention providing a biological environment having materials therein which are co-reactive with the polyvalent cation cross-linked polyelectrolyte defined herein so as to cause bioerosion thereof over a prolonged period of time.

The term "bioerode" or "dioerodible" as used in this specification and claims is intended to define a process wherein the polyvalent cation cross-linked polyelectrolytes employed and characterized in the present invention innocuously disintegrate or break down as a unit structure or entity over a prolonged period of time when placed in contact with bio-fluids by virtue of the gradual displacement of polyvalent metal ion crosslinks by non-cross-linking monovalent ions, especially sodium ions, present in the saline body fluids, with resulting solubilization of the non-cross-linked polymer. This bioerosion mechanism is especially fortuitous for erodible devices designed for the controlled release of drugs to the eye over a prolonged period of time since the conditions prevalent in the environment of the eye, e.g., tear salinity, tear flow rates, and the degree of mixing in the eye, produce polyvalent ion displacement rates, which yield erosion times for devices of a size suitable for placement in the environment of the eye from about 4 hours to about 30 days. These erosion times are perfectly suited for prolonged release ocular inserts. The erosion rate may be easily and accurately controlled within this range by varying the extent of polyvalent metal ion cross-linking, an increase in the number of polyvalent metal ion cross-links slowing the rate of bioerosion.

Another advantage of drug dispensing ocular inserts prepared from polyvalent metal ion cross-linked anionic polyelectrolytes which contain one or more drug reservoirs is their ability to advantageously administer a metered amount of drug from these reservoirs to the eye and surrounding tissues when placed in the environment of the eye. It has been found that such mode of administration surprisingly operates to significantly improve the therapeutic efficacy when compared with conventional treatment which consists of periodically applying the ophthalmic drugs in liquid or ointment form.

In preferred embodiments, the polyvalent metal ion cross-linked anionic polyelectrolyte functions in these devices or inserts as a drug release rate controlling material, controlling the administration of a metered amount of drug to the eye and surrounding tissues over a prolonged period of time when the device is placed in the environment of the eye. The polyvalent metal cation cross-linked polyelectrolytes, when used to control the rate of drug release, do so through the drug transfer mechanisms of: (1) "Permeation Control Release", i.e., the controlled release of the drug by the processes of diffusive transfer by controlled flow of drugs through the polyvalent metal ion cross-linked material, and/or "Erosion Control Release", i.e., the metered release of entrapped drug contained in the polyvalent metal ion cross-linked materials as the material bioerodes in a controlled and predetermined manner over a prolonged period of time in response to the action of the environment of the eye.

The actual control mechanism of drug release is dependent upon the design of the insert with particular regard to the combination selection of drug and release rate controlling material. In a system comprising a drug confined within a bioerodible material, two processes occur side by side: the release of drug from the material and bioerosion of the material. These two processes need not necessarily be coupled as indicated by consideration of the drug transfer mechanism above.

The following are generalized considerations to be made in order to properly design an ocular insert or for that matter any device of the types disclosed herein.

In the inventive release systems herein described, a primary factor which determines the rate of drug release is the solubility of the particular drug itself in the tear fluid impregnated microporous insert structure as later explained. Therefore, it has been found that it is not preferred to deliver water soluble drugs using the highly water permeable and hydrophilic release rate controlling polyelectrolyte materials of this invention over prolonged periods of time because the rate of release of drug is governed by that of simple rapid dissolution of the drug in tear fluid which is unsatisfactory for the reasons that the release of drug from the device is both uncontrolled and usually exceeds the desired therapeutic dosage. It is thus preferred in these cases that certain modifications be made to insolubilize or decrease the water solubility of the drug to a level at or below 50 parts per million in water so as to effect the drug release by a Permeation Control Mechanism (1), e.g., by controlled diffusive transfer. The water solubility of drug can be decreased in a number of ways, among which include the forming of pharmaceutically acceptable derivatives of the drug which have the desired solubility characteristics. These derivatives can be prepared by art known techniques and then used in the practice of the invention. Of course, the drug derivative should be such as to convert to the active drug within the body through the action of body enzymes, assisted transformation, pH, specific organ activities, and the like. Alternatively, insolubilization of the drug can be effected by coating the drug, such as by microencapsulating the drug, with a material to decrease the rate of release of drug by simple and rapid dissolution in tear fluid. Therefore, devices of the type illustrated in FIG. 3 are preferably made, in cases where the drug is water soluble by decreasing the water solubility of the drug. Methods and materials for microencapsulating the drug in order to decrease the drug solubility in water are described hereinafter with regard to the reservoirs in FIG. 6.

The rate of drug release can also be uniquely modified by varying the nature of the polyvalent metal ion cross-linked polyelectrolyte. When placed in the environment of use, e.g., the eye, the cross-linked polyelectrolytes of this invention are initially imperforate, but being hydrophilic absorb tear fluid and swell to an extent governed by their polyvalent metal cation cross-linking content to achieve fluid impregnated microporous structures. Drug can then diffuse from the internal reservoirs out through the tear fluid-filled micropores to the eye and surrounding tissues, including the corneal epithalum, by the flow of tear fluid and the blinking action of the eyelids. With Permeation Control Release, the rate of diffusion of drug through the fluid in the microporous polymeric structure controls the rate of drug release. Since by this mechanism of release the rate of drug release from the device is controlled, in addition to the solubility of the drug in tear fluid and tear layer thickness, by the porosity and swelling of the rate-controlling material, and this porosity and swelling are related to the extent of the polyvalent metal ion cross-linking in the rate-controlling material, accurate and reproducible control can be achieved by varying the degree of metal ion cross-linking.

Anionic polyelectrolyte polymeric materials which may be interacted with polyvalent cations to produce the polyvalent metal ion cross-linked structures which are employed in the present invention contain a plurality of functional groups which react with polyvalent metal cations to form water insoluble salts.

These functional groups can be characterized as being dissociable anionic groups which are chemically bonded to the polymeric chain. Suitable functional groups include carboxylic acid groups and sulfur- and phosphorous containing acid groups and their dissociable salts with monovalent cations. The anionic polyelectrolyte polymers thus include polymer chains having attached thereto a plurality of, for example, carboxylate groups, sulfonate groups, sulfate groups, phosphate groups or phosphite groups in either their acid form or monovalent cation (ammonia or alkali metal ion) form. Other non-interferring functional groups, such as hydroxyl groups, either linkages, or olefinic unsaturations, may be attached to or incorporated into the polymer chains if desired.

Exemplary anionic polyelectrolytes include modified natural and synthetic polymers such as carboxymethyl cellulose, carboxymethyl starch, polystyrene sulfonic acid, polyvinyl sulfuric acid, the sodium, ammonium and potassium salts of polyvinyl sulfuric acid, polyvinyl sulfonic acid, polyvinyl methylol sulfonic acid, polyacrylic acid, polymethacrylic acid and copolymers thereof with acrylic or methacrylic esters, polyvinyl acetate, polyvinyl alcohol, polyvinyl chloride, styrene, and as a generally preferred class of anionic polymers, the carboxyl group containing anionic polysaccharides or glycans. The polysaccharides which comprise this preferred class may contain as their dissociable anionic components, the acids D-glucuronic acid, pyruvic acid, D-mannuronic acid, D-mannopyranosyl uronic acid, D-glucopyranosyl uronic acid, D-galacturonic acid, D-guluronic acid, and L-iduronic acid; and their alkali metal or ammonium salts.

Preferred anionic polysaccharides are the naturally occurring water soluble vegetable-derived anionic polysaccharides. These include, for example, pectin, pectinic acid, pectic acid and the monovalent cation salts; the anionic exudate gums such as gum arabic, gum ghatti; the seaweed gums such as algin, alginic acid, the carrageenans and agar in acid and salt forms as well as the hemicelluloses. The anionic microbial polysaccharides such as are formed from carbon-containing substrates by the action of the microorganisms *Xanthomonas campestrix* (NRRL Strain B-1459), *Arthrobacter viscosus* (NRRL Strain B 1973) or *Cryptococcus laurentii* (NRRL Strain Y 1401) may also be employed to advantage.

The naturally-occurring vegetable-derived water-soluble polysaccharides are preferred as they are essentially devoid of human or animal toxicity and undergo enzymatic cleavage in the body to easily absorbed simple sugars.

The initially water soluble anionic polyelectrolytes are cross-linked with polyvalent metal cations to yield the drug release controlling materials of this invention. In general, any polyvalent metal cation which is non-toxic to the mammalian patient being treated may be used. Preferred cations include the non-toxic polyvalent cations of elements of atomic number 13 through 56 inclusive which are found in groups IIa through IIIa inclusive of the Periodic Table of the Elements such as barium II, copper II, iron II and III, zinc II, aluminum III and cadium II. A preferred group of these metals comprises calcium II, barium II, zinc II and aluminum III.

The amount of polyvalent ion cross-linking should be controlled since it can determine to a major extent the drug permeability and hence drug release characteristics of the polyelectrolyte product. As a rule, increasing the amount of metal ion increases the amount of cross-linking and lowers the drug release rate. It is generally suitable to employ from about 0.2 to 3 equivalents of polyvalent cation for each equivalent of polyelectrolyte anionic groups capable of cross-linking. It is preferred to employ from about 0.4 to about 1.5 equivalents of polyvalent metal cation for each equivalent of polyelectrolyte anionic groups. The exact proportions of polyvalent cation employed should be controlled to tailor the precise drug release rate desired.

Polyvalent metal cation cross-linked anionic polyelectrolytes for use as drug release controlling materials can be prepared by several alternative methods. As a general rule, these materials are not easily shaped or formed when in their cross-linked configuration, so it is desirable to form or shape the polyelectrolyte in a non-cross-linked form and carry out the cross-linking.

One very suitable method for preparing the polyvalent metal ion cross-linked product comprises: (a) In a first step preparing an aqueous first solution containing an initially water-soluble anionic polyelectrolyte and adding thereto a polyvalent metal cation, to form a water insoluble metal cross-linked precipitate. The concentration of the anionic polyelectrolyte in the first solution prior to precipitation is not critical and may vary from about 0.01% by weight to its solubility limit. The cross-linked precipitate should be washed free of monovalent cations. For example if the initial soluble polyelectrolyte was sodium alginate and it was treated with calcium ions to yield a calcium cross-linked alginate precipitate, the sodium ion should be washed from the precipitate. If this is not done, the rate of bioerosion, which is in part controlled by the displacement of polyvalent cross-linking ions with monovalent non-cross-linking ions from tear fluids, may be irreproducible because of the availability of residual monovalent ions in the precipitate itself. The amount of polyvalent metal ion containing precipitate should be closely controlled since any polyvalent metal ion introduced into the system during this precipitation, unless in such excess as to be rinsed out in the washing steps, will appear in the final product as cross-linking. As already noted, the rate of drug release is a function of the extent of polyvalent metal ion polyelectrolytes cross-linking. (b) In a second step, adding to the water-insoluble cross-linked precipitate a sufficient amount of a complexing reagent to render the precipitate water-soluble by forming a water soluble coordination complex with the polyvalent metal cations. Suitable complexing reagents are any of those materials which are capable of solubilizing or maintaining the polyelectrolyte-polyvalent cationic reaction product in solution so as to enable fabrication of the solution into the desired shape. Electron donating complexing reagents are generally preferred. Exemplary of electron donating materials are primary, secondary and tertiary amines such as mono, di, or trimethyl amine, mono, di, or tri-ethanolamine, morpholine, pyridine, piperidine, piperazine, aniline, 2-methyl imidazole, ethylene diamine and higher polyethylene polyamines, and amonia.

The complexing reagent must be present in solution in an amount sufficient to prevent precipitation of the reactive components. This amount will usually be from about 0.5 to 10 moles of complexing reagent per gram atom of polyvalent metal ion, and preferably is from 1 to 5 moles of complexing reagent per gram atom of polyvalent metal. Although amounts as great as 50% or more weight of the total solution may be used, it is unnecessary and frequently undesirable to employ any more than the minimum amount of complexing reagent required to prevent precipitation of the polyelectrolytes. In general, the concentration of the polyelectrolyte in the resulting solution must be at least 0.5% by weight and preferably above 1% by weight, based on the solution in order to obtain continuous solids in the supsequent processing.

In a third step, the aqueous solution is formed into the dsired shapes and configurations. This forming may be carried out by casting, extruding, coating and like techniques. If desired, drugs may be dispersed or dissolved in the solution at this point.

In a fourth step, the solution thus formed is then caused to gel by changing conditions so as to permit precipitation to occur by breaking down the coordinate complex so as to cross-link the polymer with metal. Gelation of the polymeric complex solute can be effected by reducing the effective concentration of the complexing reagent by neutralization thereof with acid, or removal in the case of volatile reagents by evaporation in the presence of heated moist air. The formed structure of polyvalent metal ion cross-linked polyelectrolyte is then recovered.

In an alternative method of production, the complexing reagent can be added to the solution of anionic polyelectrolyte prior to the addition of the polyvalent cation to maintain the reaction product in solution in lieu of resolubilizing the precipitate. This method comprises the sequential steps of: fabricating a solution of an initially water-soluble anionic polyelectrolyte and optionally drugs into the desired shape; in a second step dipping the thus formed shape into an aqueous solution of a polyvalent metal cation to cross-link the anionic polyelectrolyte; and finally recovering the thus prepared water insoluble cross-linked structure. Undesired monovalent cations of present are then removed by washing during the recovery step.

It is often desired to incorporate plasticizers in the polyvalent metal ion cross-linked polyelectrolyte materials to improve or vary their physical properties, such as to make them more flexible. Exemplary plasticizers suitable for employment for the present purpose are the pharmaceutically acceptable plasticizers conventionally used, such as diethyl adipate, di-isobutyl adipate, di-n-hexyl adipate, di-isooctyl adipate di-n-hexyl azelate, di-2-ethyl-hexylazelate, ethylene glycol dibenzoate, acetyl tri-n-butyl citrate, epoxidized soy bean oil, glycerol monoacetate, diethylene glycol dipelargonate, propylene glycol diluarate, isooctyl palmitate, triphenyl phosphate, and the like. In addition, binding agents or disintegrating agents to regulate or to facilitate the bioerosion of the device can be employed. Exemplary of these materials are glycerin, dextrose, sorbitol, mannitol, sucrose, poly(ethylene glycol), monoglyceryl esters of fatty acids, methylcellulose, starch, and the like. The proportion of agent used will vary within broad limits depending upon the rate of disintegration desired, as well as upon the characteristics of the medicament and metal ion cross-linked polyelectrolyte involved. In general, about 0.01 parts to about 5 parts by weight for each part by weight of the polyelectrolyte can be used, depending on the agent.

Enzymes can be incorporated into the release rate controlling materials in order to further control their rate of bioerosion. when plasticizers, enzymes, etc. are included in the metal ion cross-linked polymers they are most suitable added prior to shaping the final formed structure, such as by dissolving or dispensing them in the solution from which the body is gelled.

The metal ion cross-linked anionic polyelectrolytes may be employed in all types of devices for delivering drugs to the eye. While not intending to restrict the scope of this invention certain embodiments of bioerodible drug releasing devices employing these metal ion cross-linked polyelectrolytes and their use in dispensing drug to the eye are exemplified in the drawings which are exaggerated in size for purposes of illustration.

Figure 1:
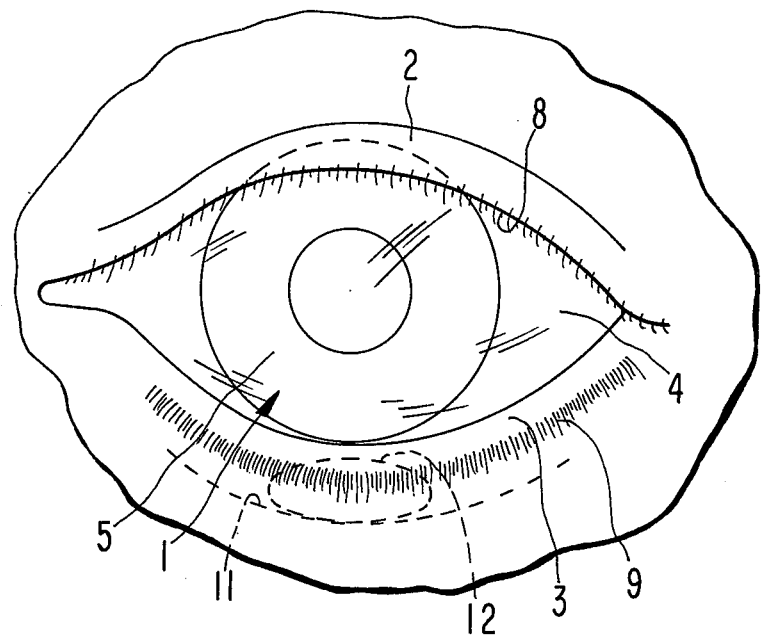
FIG. 1 is a view partly in front elevation and partly diagrammatic of a human eye, illustrating an ocular insert of this invention in an operative position after insertion in the eye.
Figure 2:
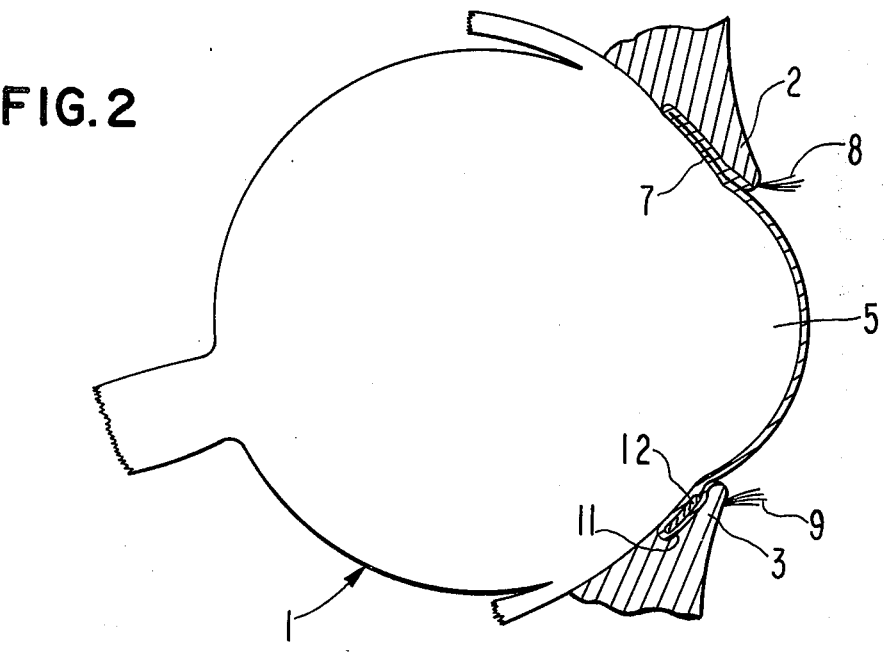
FIG. 2 is a view partly in vertical section and partly diagrammatic of an eyeball and the upper and lower eyelids associated therewith showing the ocular insert of this invention in operative position.

Referring particularly to FIGS. 1 and 2, a human eye is shown in each figure, more or less diagrammatically, comprising an eyeball 1 and upper and lower eyelids 2 and 3, respectively, the eyeball 1 being covered for the greater parts of its area by the sclera 4 and at its central portion by the cornea 5. The eyelids 2 and 3 are lined with an epithelial membrane or palpebral conjunctiva. The sclera 4 is lined with the bulbar conjunctiva which covers the exposed portion of the eyeball. The cornea 5 is covered with an epithelial layer which is transparent. That portion of the palpebral conjunctiva which lines the upper eyelids 2 and the underlying portion of the bulbar conjunctiva defines the upper sac 7 and that portion of the palpebral conjunctiva which lines the lower eyelid 3 and the underlying portion of the bulbar conjunctiva defines the lower sac 11. Upper and lower eyelashes are indicated at 8 and 9, respectively.

A bioerodible ocular insert 12 in accord with this invention is shown in operative position in the lower sac 11 of the eye. Other details of the eyeball 1 are not directly concerned with the structure of the instant invention and, therefore, details showing the description thereof are being omitted in the interest of brevity. To use the ocular insert of the invention, it is inserted in the eye, preferably within the upper sac 7 or lower sac 11, bounded by the surfaces of the sclera of the eyeball and the conjunctiva of the lid. Insertion of the insert 12 into the eye can be satisfactorily accomplished by mounting or grasping the device by means of a suitable holder, which optionally may include a minute suction cup for engaging the outer surface of the insert. The holder may be one of the several types commonly used to insert and remove corneal contact lenses, artificial eyes, and the like. Once in place, the ocular insert functions to administer a metered amount of drug from the reservoir to the eye and surrounding tissues, in preferred embodiments, continuously over a prolonged period of time.

Figure 3:
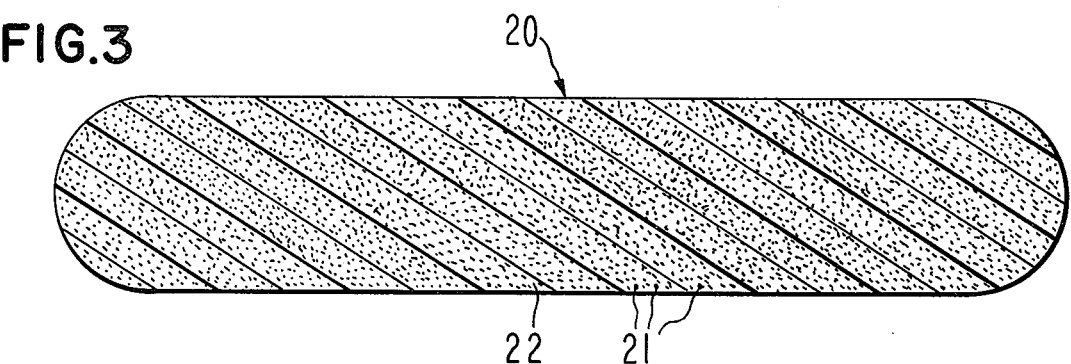
FIGS. 3, 4, 5 and 6 are diagrammatic cross-sectional views of several embodiments of ocular inserts of this invention.

FIGS. 3 to 6 inclusive, illustrate, in diagrammatic cross-sectional views, exemplary types of drug dispensing ocular inserts which employ polyvalent metal ion cross-linked anionic polyelectrolytes. FIG. 3 illustrates generally, by reference numeral 20, an embodiment of this invention wherein the bioerodible ocular insert is comprised of a continuous matrix 22 formed of polyvalent metal ion cross-linked anionic polyelectrolytes that have particles of drug 21 dispersed therethrough. The matrix 22 functions both as a drug reservoir and a rate-controlling material. When ocular device 20 is placed in the environment of the eye it absorbs tear liquid and swells, achieving a microporous structure which is permeable to drug. Drug 21 can continuously diffusively transfer through these micropores in a permeation control mode of release, the rate of drug release being primarily dependent upon the extent of polyvalent metal ion cross-linking in the material of matrix 22 and the solubility of drug in the eye fluids impregnated in the structure. If the drug is water soluble, this mode of release is not preferred and other embodiments of this invention, to be set forth hereinafter, are generally better suited for delivery by the water soluble drugs.

The ocular insert can be fabricated in any convenient shape for comfortable retention in the sac of the eye. Thus, the marginal outline of the ocular insert can be ellipsoid, donut-shape, bean-shape, banana-shape, circular, retangular, etc. In cross-section, it can be doubly convex, concavo-convex, rectangular, etc. as the ocular insert in use will tend to conform to the configuration of the eye, the original cross-sectional shape of the device is not of controlling importance. Dimensions of the device can vary widely. The lower limit on the size of the device is governed by the amount of the particular drug to be supplied to the eye and surrounding tissues to elicit the desired pharmacologic response, as well as by the smallest sized device which conveniently can be inserted in the eye. The upper limit on the size of the device is governed by the geometric space limitations in the eye, consistent with comfortable retention of the ocular insert. Satisfactory results can be obtained with an ocular device for insertion in the sac of the eye of from 4 to 20 millimeters in length, 1 to 12 millimeters in width, and 0.1 to 2 millimeters in thickness.

Figure 4:
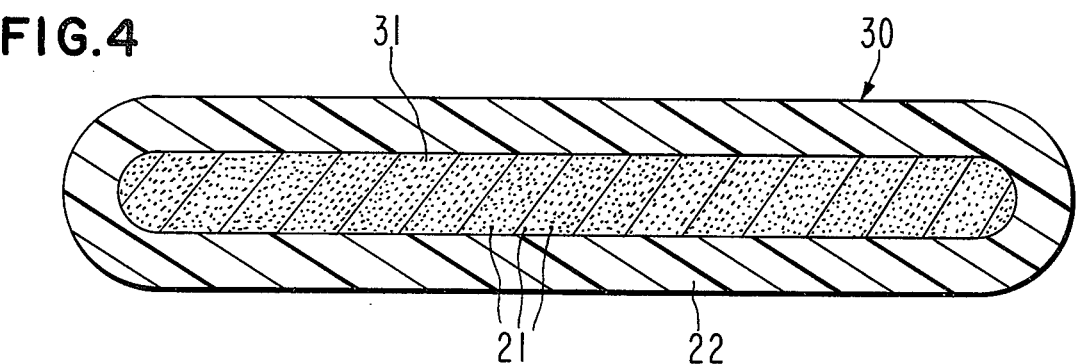

FIG. 4 illustrates generally, by reference numeral 30, an embodiment of this invention which finds its most general application for the release of water insoluble drugs. The bioerodible ocular insert is comprised of an inner reservoir 31 which is formed of a biodegradable matrix material having drug 21 dispersed therethrough. Surrounding matrix 20 is bioerodible rate controlling membrane 22 constructed of the polyvalent metal ion cross-linked polyelectrolyte in accord with the invention. Both matrix 20 and membrane 22 are permeable to the passage of drug by diffusion, that is, molecules of the drug can dissolve in and diffuse through these materials; however, the permeability of membrane 22 to drug is lower than from the matrix 31 so that release of drug through membrane 22 is the drug release rate controlling step from the ocular insert. The inner matrix 31 serves as a depot or reservoir source for the drug and can be a porous, solid or gel material. When ocular insert 19 is placed in the eye, drug is continuously metered through and removed from the outer surface of bioerodible membrane 22 where it is made available to the eye fluids and tissues.

An advantage of the insert of the type illustrated in FIG. 4 is that it can be adapted to release drug in a zero order manner, that is, at a constant rate and over a prolonged period of time. By the appropriate design and selection of materials, drug release from the device is preferably primarily effected by a "permeation control release mechanism" and includes a sequence of steps characterized by controlled drug diffusion through the pore filled medium of the metal ion cross-linked polyelectrolyte membrane 22 followed by a combination of leaching of drug by the tear liquid and the blinking action of the eyelids in order to transport the drug from the outermost surface of membrane 22 to the eye and surrounding tissues. Release rate is controlled by system variables such as the diffusivity and solubility of the drug in the pore filled medium of the cross-linked polyelectrolyte membrane 22, the thickness of this membrane. Design of an ocular device, therefore, necessitates selection of materials and other parameters in order to provide the proper release rates and dosage regimen, depending upon the particular drug to be used. The following are generalized considerations in order to properly design an ocular insert of the type illustrated in FIG. 4.

The mechanism by which diffusion is achieved may be explained on the basis of an activity or chemical potential gradient wherein the confined drug relieves its internal concentration by spreading out into the adjacent medium. As the drug is removed from the device and absorbed by eye tissues or carried away by the eye fluids, the diffusive action continues until the source of drug 21 has been substantially consumed. The drug will have a defnite and characteristic rate of passage through the release rate controlling cross-linked polyelectrolyte membrane of the insert. It is preferred, although not essential, that drug 21 essentially be depleted or consumed from the reservoir 31 before release rate controlling membrane 22 completely bioerodes. However, if it is desired to obtain a constant rate of drug release rate over the active releasing period of the insert, prior depletion of drug is an essential requirement. Upon the erosion of membrane 22, reservoir 31 will erode as well, leaving no residual parts in the eye to be removed.

The reservoir 31 primarily functions as a depot for the drug rather than as a rate control barrier. Therefore, it should be highly permeable to passage of drug by diffusion. In contrast, membrane 22 which acts as the rate-limiting barrier to control drug release must be only slowly permeable to the passage of drug, with the exact value determined by the desired release rate. Thus, it is important to the achievement of a constant rate of release that the membrane 22 have a lower permeability to the drug by diffusion than does the matrix material 31. The initial ratio of permeability rates for drug for the matrix material 31 to membrane material 22 should be approximately between 1.5:1 and 100:1, and preferably between 2:1 and 10:1. It is preferred, in order to obtain zero order drug release, that the drug be sparingly soluble in the reservoir matrix material so as to retain substantially the same thermodynamic activity of the drug throughout the release period. By "sparingly soluble" is meant that the fractional amount of drug dissolved in the reservoir material should be in the range of from 0.1% to 35% by weight of the total amount of drug to be delivered, such that solid particles of drug are present throughout most of the drug release period. Moreover, for best results, the rate of passage of drug through membrane 22 should not exceed the rate of removal or clearance of drug from the exterior of the membrane by eye tissues. This insures that the drug delivery rate is controlled by diffusion through the polyvalent metal ion cross-linked polyelectrolyte membrane 22, which can be controlled.

As discussed above, the selection of appropriate materials for fabricating the ocular inserts will be dependent upon their erosion rates in the eye. The erosion rate of outer membrane material 22 in the eye is determined by the desired ophthalmic dosage regimen, as well as the length of time the device is to remain in the eye. Under optimum conditions, the erosion rate should be such that substantially all of the membrane material 22 bioerodes in the eye tissue soon after the drug has been substantially depleted from the reservoir 20, preferably no later than in a period of from 24 hours thereafter, if possible.

In general, to design a device of the type shown in FIG. 4 it is first necessary to select the drug to be used, its disage, and the period of therapy. This establishes the required drug release rate and amount of drug to be incorporated in the device. Materials for both the reservoir and rate controlling polyvalent metal ion cross-linked polyelectrolyte membrane which have the appropriate permeability characteristic and erosion and degration rates can then be correlated with thickness and effective surface release area to fabricate a device which meters the desired amount of drug to the eye over the established period of time and thereafter completely erodes in the eye.

Figure 5:
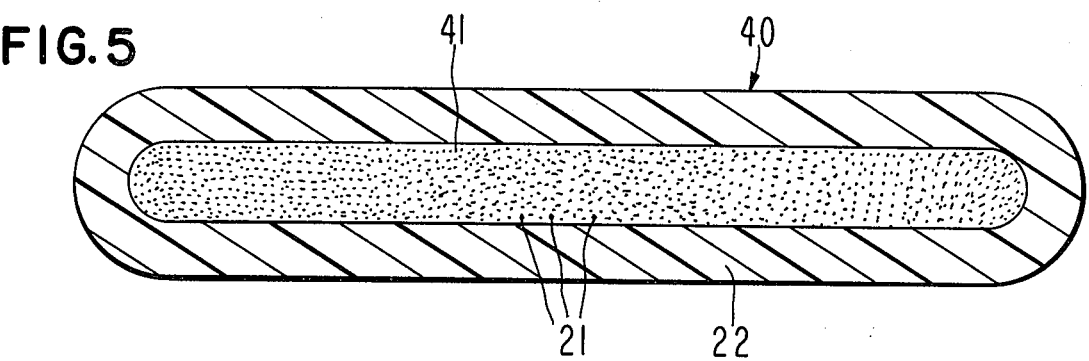

FIG. 5 illustrates generally, by reference numeral 40, another bioerodible ocular insert of this invention having a hollow interior reservoir 41 containing drug formulation 21 in the reservoir 41. Polyvalent metal ion cross-linked anionic polyelectrolyte rate controlling bioerodible membrane 22 surrounds the reservoir 40 and controls the flow of drug from the reservoir 41 to the eye. This embodiment differs from that illustrated in FIG. 4, mainly in that therein the reservoir 31 is formed of a matrix material with the drug dispersed therethrough, whereas in the embodiment of FIG. 5 the drug 21 is confined in the hollow reservoir container 41. The insert shown in FIG. 5 operates in a manner similar to the device illustrated in FIG. 4, as described above. It is imperative that the drug 21 be depleted from the reservoir 41 prior to the complete erosion of rate conrolling membrane 22 in order to avoid a sudden and unwanted release of drug from the reservoir 41 to the eye.

When the drug being released to the eye is water soluble, it is often difficult to control its rate of release with the hydrophilic polyvalent metal ion cross-linked anionic polyelectrolytes of the present invention. In such cases the rate of drug release may be provided by simple rapid dissolution of the drug in tear fluids which is unsatisfactory for the reasons that the release of drug is both uncontrolled and usually exceeds the desired therapeutic dosage. It is therefore preferred in these cases when employing the embodiment of FIG. 4 that certain modifications be made to insolubilize or decrease the water solubility of the drug so as to effect the drug release by a Permeation Control mechanism, e.g., by controlled viscous fluid diffusive transfer as hereinbefore discussed.

Figure 6:
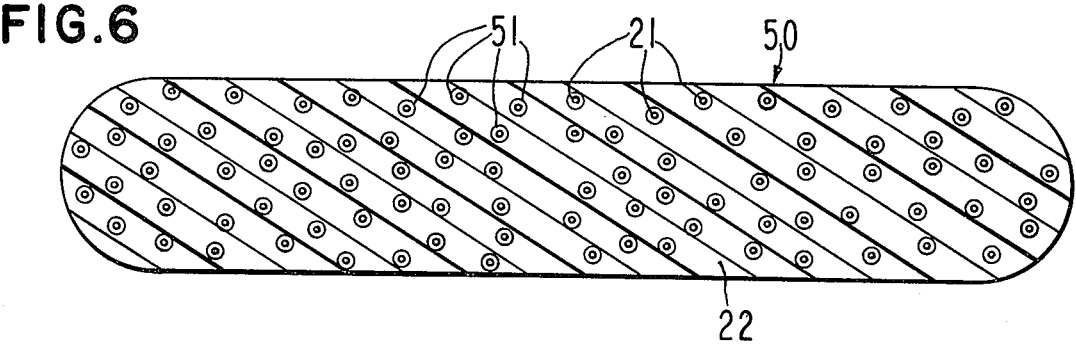

FIG. 6 illustrates an ocular insert 50 of this invention particularly suited for administering a water soluble drug. The drug delivery device 50 is comprised of a bioerodible matrix 22 of polyvalent cation cross-linked anionic polyelectrolyte material having dispersed therethrough a plurality of drug reservoirs 51. The reservoirs 51 are microcapsules comprised of a water soluble drug whether in solid form, liquid form or in admixture with a carrier, confined within a drug release rate controlling material. Drug molecules released from the reservoirs 51 pass into the matrix 22 and then migrate through the matrix 22 for administration of drug to the eye. Release of drug from the reservoir is the rate controlling step for release of drug from the device. In construction, the device can be viewed as a single unit device comprising two structures acting in concert for effective drug administration to the eye. One structure pertains to the reservoirs 51 which are microcapsules comprising a microbody of drug release rate controlling material having drug 21 confined therein, and the other structure relates to the bioerodible matrix 22 housing the reservoirs and is formed of a material permeable to the passage of drug.

The reservoirs 51 can be formed as a hollow container having a drug therein formed from drug release rate controlling material. Additionally, the reservoir 51 can be a solid particle having a drug distributed therethrough and formed of a drug release rate controlling material. Alternatively, the reservoir 51 can be a porous structure formed of a material possessing drug release rate controlling properties. Reservoir 51 can have the conventional aggregate structure and particulate structure of conventional geometric shape. By controlling the structure of the reservoirs of the drug delivery device, the invention makes possible a drug time pattern of release, including a zero order drug release. Thus, in the presently preferred embodiments for obtaining a constant rate of release, the reservoir is formed as a capsule containing the drug therein and surrounded by a rate controlling membrane, or the reservoir is a solid matrix with a limited number of discrete particles of drug contained therein.

The materials suitable for fabricating the reservoir 51, whether of hollow, solid, porous, semi-porous or the like structures, are generally those materials capable of forming membranes with or without pores or voids, or coating through which the drug can pass at a controlled rate by the process of diffusion. Suitable materials for forming the reservoirs are naturally - occurring or synthetic materials that are non-toxic and whidh preferably have a low solubility and/or low diffusivity to water. In general, these qualities will be possessed by rate release controlling materials that are hydrophobic in nature. The rate controlling materials used for the reservoir 51 can be biodegradable, biodegradation in the environment of the eye taking place concurrently with the dispensing or at a point in time after the dispensing of the therapeutically desired amount of drug. Alternatively, when the reservoir 51 is of an initial size and configuration such as to be capable of being eliminated from the ocular cavity through the punctum with tear fluid can be made of non-biodegradable material. Microcapsules, preferably of approximately 100 micron size or less, will be of suitable dimension for proper punctum passage.

Exemplary non-biodegradable materials suitable for fabricating the microcapsules when of an initial size such as to pass through the punctum are drug release rate controlling materials such as hydrophobic polymers, e.g., polyvinylchloride, nylon, silicon rubber, cholesterol; substituted alkyl celluloses such as hydroxypropyl methyl cellulose, methyl cellulose, ethyl cellulose, cellulose acetate; waxes, e.g., paraffin, ethylene wax, hydrogenated castor oil; $C_{10}$ to $C_{20}$ fatty acids, e.g., stearic acid, palmitic acid; hydrophilic polymers, e.g., polymerized esters of methacrylic acid (Hydron), and the like. Biodegradable materials suitable for preparing the microcapsule reservoirs are disclosed hereinafter. The actual material selected for fabricating the microcapsule reservoir is one that can slow down the rate of release of the water soluble drug to the desired level. Preferred are the hydrophobic materials. Although hydrophilic type materials can sometimes be employed for fabricating the reservoir in cases where the water soluble drug is not too highly permeable therein, in most cases thicker coatings of microcapsule material and larger microcapsule diameters will be required than for hydrophobic type microcapsule materials. In this regard, among other factors which must be considered, in addition to the nature of the reservoir rate controlling material, and which effect the rate of release of drug from the microcapsule, are the microcapsule size, the density of drug and the thickness of the reservoir wall. Qualitative guides in this regard are that the rate of release of drug will decrease with corresponding increasing values for each of these parameters as will be appreciated by those skilled in the art.

Any of the standard encapsulation or impregnation techniques known in the art can be used to prepare the microcapsules 51 to be incorporated into the matrix material 22, of FIG. 6, in accord with this invention. Thus, the drug, admixture of drug, or drug solution can be added to the encapsulating material in liquid form and uniformly distributed therethrough by mixing; or solid encapsulating material can be impregnated with the drug by immersion in a bath of the drug to cause the drug to diffuse into the material. Subsequently, the solid material can be reduced to fine microcapsules by grinding, each of the microcapsules comprising drug coated with and distributed throughout the encapsulated material. Alternatively, fine particles or solutions of the drug can be encapsulated with a coating. One suitable technique comprises suspending dry particles of the drug in an air stream and contacting that stream containing the encapsulating material that coats the drug with a membrane permeable to drug.

Another standard method of microencapsulation suitable for the purpose of the invention is the coacervation technique. The coacervation technique of fabrication as conventionally employed consists essentially of the formation of three imiscible phases, a liquid manufacturing phase, a core material phase and a coating phase with deposition of the liquid polymer coating on the core material and rigidizing the coating, usually by thermal, cross-linking or desolvation techniques to form microcapsules. Techniques for preparing microcapsules, such as the classic Bungenberg de Jong and Kaas method are reported in *Biochem. Z.*, Vol. 232, pp. 338–345, 1971; *Colloid Science*, Vol. 11, "Reversible System", edited by H. R. Kruyt, 1949, Elsevier Publishing Company, Inc., New York; *J. Pharm. Sci.*, Vol. 59, No. 10, (1970), pp. 1367–1376; and, *Remington's Pharmaceutical Science*, Vol. XIV, Mack Publishing Company, Easton, Pa., 1970, pp. 1676–1677. Other procedures for preparing microcapsules are set forth in West German Patent No. DT-1939-066; and the like.

Although the device of the type illustrated in FIG. 6 is particularly well suited to the administration of water soluble drug and so described above, it will be appreciated that it is equally well adapted to the administration of drugs as hereinafter set forth which are not water soluble.

Devices of the type shown in FIG. 6 can be designed by first selecting the drug to be used, its dosage, and the period of therapy. This establishes the required drug release rate and amount of drug to be incorporated in the device. Materials having the appropriate drug release rate characteristics and erosion rates can then be correlated with the effective surface release area to fabricate a device which meters the desired rate of the drug to the eye over the established period of time. A particular added advantage of a device of the type as illustrated in FIG. 6 is the fact that the number of reservoirs employed can be varied in order to achieve the desired drug release rate from the device.

Any of the drugs used to treat the eye and surrounding tissues can be incorporated in the ocular insert of this invention. Also, it is practical to use the eye and surrounding tissues as a point of entry for systemic drugs or antigens that ultimately enter circulation in the blood stream, or enter the nasopharyngeal area by normal routes, and produce a pharmacologic response at a site remote from the point of application of the ocular insert. Thus, drugs or antigens which will pass through the eye or the tissue surrounding the eye to the blood stream or to the nasalpharyngeal, esophageal or gastrointestinal areas, but which are not used in therapy of the eye itself, can be incorporated in the ocular insert.

Suitable drugs for use in therapy of the eye with the ocular insert of this invention consistent with their known dosages and uses are without limitation: antibiotics such as tetracycline, chlorotetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antivirals, including idoxuridine; and other antibacterial agents such as nitrofurazone and sodium propionate; antiallergenics such as antazoline, methapyriline, chlorpheniramine, pyrilamine and prophenpyridamine; anti-inflammatories such as hydrocortisone, hydrocortisone acetate, dexamethasone, dexamethasone 21-phosphate, fluocinolone, medrysone, prednisolone, methylprednisolone, predisolone 21-phosphate, prednisolone acetate, fluoromethalone, betamethasone and triamcinolone; decongestants such as phenylephrine, naphazoline, and tetrahydrazoline; miotics and anticholinesterases such as pilocarpine, eserine salicylate, carbachol, di-isopropyl fluorophosphate, phospholine iodide, and demecarium bromide; mydriatics such as atropine sulfate, cyclopentolate, homatropine, scopolamine, tropicamide, eucatropine, and hydroxyamphetamine; and sympathomimetics such as epinephrine.

Drugs can be in various forms, such as uncharged molecules, components of molecular complexes, or non-irritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs such as ethers, esters, amides, etc., which have desirable retention, release or solubility characteristics, but which are easily hydrolized by body pH, enzymes, etc., can be employed. The amount of drug incorported in the ocular insert varies widely depending on the particular drug, the desired therapeutic effect, and the time span for which the ocular insert will be used.

The above drugs and other drugs can be present in the reservoir alone or in combination form with pharmaceutical carriers. The pharmaceutical carriers acceptable for the purpose of this invention are the art-known carriers that do not adversely affect the drug, the host, or the material comprising the drug delivery device. Suitable pharmaceutical carriers include sterile water; saline; dextrose; dextrose in water or saline; condensation products of castor oil and ethylene oxide combining about 30 to about 35 moles of ethylene oxide per mole of castor oil; liquid glyceryl triester of a lower molecular weight fatty acid; lower alkanols; oils such as corn oil; peanut oil, sesame oil, and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrrolidone); and the like, alone, or with suitable dispensing agents such as lecithin; polyoxyethylene stearate; and the like. The carrier may also contain adjuvants such as preserving, stabilizing, wetting, emulsifying agents, and the like.

To provide compatibility with the eye and surrounding tissues, at least for the initial period after insertion, the surface of the ocular insect in contact with the eye can be coated with a thin layer, e.g., from 1 to 2 microns thick, biodegradable hydrophilic material. Exemplary of the suitable materials for this purpose are gelatin, non-cross-linked polysaccharides, and the biodegradable materials disclosed in British Patent No. 1,372,944 which patent is the convention applicaton of U.S. Patent application Ser. No. 179,129 filed on Sept. 9, 1971 by Higuchi, T., Hussain, A, and Shell, J., and assigned to the same assignee as this application. Exemplary materials disclosed in the patent and incorporated herein by reference include glycerinated gelatin, collagen, gum acacia, polyvinyl alcohol, polyvinyl pyrrolidone, alginic acid and alkali metal salts of alginic acid, starch phosphate, starch e.g., agar, gum arabic, and the like.

In preferred embodiments, the ocular insert is intended to provide a complete dosage regimen for eye therapy over this prolonged period. Therefore, the amount of drug to be incorporated in the device is determined by the fact that sufficient amounts of drug must be present to maintain the desired dosage level over the therapeutic treatment period. Typically, from 1 microgram to 1 gram or larger of drug is incorporated in the ocular insert, the exact amount, of course, depending upon the drug used and treatment period. Illustratively, in order to treat glaucoma in an adult human, the daily release dosage should be in the range of between 25 micrograms to 1000 micrograms of pilocarpine per day. Thus, for example, using pilocarpine with a device intended to remain in place for 7 days, and with a release rate of 500 micrograms of drug per day, 3,5 milligrams of pilocarpine will be incorporated in the device. Other devices containing different amounts of drug for use for different time periods and releasing drug at higher or lower controlled rates are also readily made by the invention.

Further, in practicing this invention one can employ any of the aforementioned listed drugs, consistent with their known dosages and uses, to establish a release rate, e.b., micrograms/insert/day. Exemplary of the dosages to be used are:

| | |
|---|---|
| Antibiotics, such as polymixin: | 250 micrograms/insert/day |
| Sulfonamides, such as sulfacetamide: | 500 micrograms/insert/day |
| Antivirals, such as idoxuridine: | 5 micrograms/insert/day |
| Anti-inflammatories, such as hydrocortisone acetate or prednisolone: | 500 micrograms/insert/day |

The ocular inserts are suitably packaged using a drug and moisture impermeable packaging material such as the foil-polylaminates, e.g., aluminum foil-polyethylene laminate or aluminum foil-polyester (Mylar)-laminate. While the inserts can be packaged either wet or dry, the latter becomes mandatory when certain bioerosion processes are involved. More specifically, when the bioerosion process is effected by dissolution or hydrolysis, dry packing, e.g., vacuum packing, is required.

The ocular devices are preferably sterilized prior to insertion in the eye. The sterilization can be effected prior to packaging or after packaging. Suitable sterilization methods such as the use of radiation or ethylene oxide can be satisfactorily employed. Details for these methods and others are set forth in *Remington's Pharmaceutical Sciences*, Vol. XIV, 1970, pp. 1501–1518.

Essential to this invention is the use of polyvalent metal ion cross-linked anionic polyelectrolyte materials for the controlled administration of drug to a patient. Although the use of polyvalent metal ion cross-linked anionic polyelectrolytes in drug delivery devices has principally been described with regard to erodible ocular devices for the controlled administration of drugs to the eye, these materials may be employed as well in a wide variety of bioerodible devices for administering drugs at controlled rates to other areas of the body which offer a saline environment as is required to effect bioerosion. Thus various other forms of the invention are intended to be included herein. Thus, the metal ion cross-linked polyelectrolytes may be employed to advantage in external and internal erodible drug delivery devices such as, for example, buccal patches, sublingual or bucal tablets, peroral dosage forms which bioerode by the action of the saline in saliva; subcutaneous implantates for releasing a drug to the tissues of a patient; artificial glands, which are eroded by salinity of blood; vaginal suppositories, drug dispensing intrauterine devices; and rectal suppositories which are eroded by the action of vaginal and intestinal fluids respectively. In each instance, the device employs polyvalent metal ion cross-linked anionic polyelectrolytes and is of a shape or form appropriate for implementation or insertion in the described body tissues or cavities, respectively or for application to a particular body area.

Therefore in practicing the invention, one can employ any drug used to treat the body in addition to those ophthalmic drugs previously listed, which is capable of being dispersed in or confined by the polymer in accordance with its known usage. The term "drug" as used herein is intended to be interpreted in its broadest sense as including any composition or substance that will produce a pharmacologic response either at the site of application or at a site remote therefrom. Suitable drugs for use in therapy with the drug delivery system of the invention include, without limitation:

1. Protein drugs such as insulin;
2. Desensitizing agents such as ragweed pollen antigens, hay fever pollen antigens, dust antigen and milk antigen;
3. Vaccines such as small pox, yellow fever, distemper, hog cholera, fowl pox, anti-venom, scarlet fever, diphtheria toxoid, tetanus toxoid, pigeon pox, whooping cough, influenzae, rabies, mumps, measles, poliomyelitis, Newcastle disease, etc.;
4. Anti-infectives, such as antibiotics, including penicillin, tetracycline, chlortetracycline, bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiazine, sulfamerazine, and sulfisoxazole; anti-virals including idoxuridine; and other anti-infectives including nitrofurazone and sodium propionate;
5. Anti-allergenics such as antazoline, methapyrilene, chlorpheniramine, pyrilamine, and prophenpyridamine;
6. Anti-inflammatories such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;
7. Decongestants such as phenylephrine, naphazoline, and tetrahydrozoline;
8. Sympathomimetics such as epinephrine;
9. Sedatives and Hypnotics such as pentobarbital sodium, phenobarbital, secobarbital sodium, codeine, ($\alpha$-bromoisovaleryl) urea, carbromal;
10. Psychic Energizers such as 3-(2-aminopropyl) indole acetate and 3-(2-aminobutyl) Indole acetate;
11. Tranquilizers such as reserpine, chloropromazine, and thiopropazate;
12. Androgenic steroids such as methyltestosterone and fluoxymesterone;
13. Estrogens such as estrone, 17 $\beta$-estradiol, ethinyl estradiol, and diethyl stilbesterol;
14. Progestational agents such as progesterone, megestrol, melengestrol, chloromadinone, ethisterone, norethynodrel, 19-nor-progesterone, norethindrone, medroxyprogesterone and 17 $\alpha$-hydroxyprogesterone;
15. Homoral agents such as the prostaglandins, for example, $PGE_1$, $PGE_2$, and $PGF_2$;
16. Antipyretics such as aspirin, sodium salicylate, and salicylamide;
17. Antispasmodics such as atropine, methantheline, papaverine, and methscopolamine bromide;
18. Anti-malarials such as the 4-amino-quinolines, 8-aminoquinolines, chloroquine, and pyrimethamine;
19. Antihistamines such as diphenhydramide, dimenhydrinate, tripelennamine, perphenazine, and carphenazine;
20. Cardioactive agents such as hydrochlorothiazide, flumethiazide, chlorothiazide, and aminotrate;
21. Nutritional agents such as vitamins, essential amino acids and essential fats;
22. Anti-Parkinsonism agents such as L-dopa, (L-3,4-dihydroxyphenylalanine);
23. Investigative antihypotensive agents such as dopamine, 4-(2-aminoethyl) pyrocatechol.

Other drugs having the same or different physiological activity as those recited above can be employed in drug delivery systems within the scope of the present invention. Suitable mixtures of drugs can, of course, be dispensed with equal facility as with single component systems.

Drugs can be in different forms, such as uncharged molecules, components of molecular complexes, or non-irritating, pharmacologically acceptable salts such as hydrochloride, hydrobromide, sulfate, phosphate, nitrate, borate, acetate, maleate, tartrate, salicylate, etc. For acidic drugs, salts of metals, amines, or organic cations (e.g., quaternary ammonium) can be employed. Furthermore, simple derivatives of the drugs (such as ethers, esters, amides, etc.) which have desirable retention and release characteristics but which are easily hydrolyzed by body pH, enzymes, etc. can be employed.

The amount of drug employed in devices in accord with this invention may vary over a wide range, depending upon the type of drug and the dosage desired and the size and type of device in which the drug is employed. The amount may vary from the minimum effective single dosage of the drug employed to a maximum number of effective doses limited by the size and/or erosion characteristics of the devices. In general, drug is usually present in an amount equivalent to from about 5% to 90% of the weight of the polyvalent metal ion cross-linked polyelectrolyte, although larger or smaller amounts consistant with the above noted general limits may be employed if desired.

The rate of bioerosion or biodegration of materials employed in the invention can be determined experimentally by placing them under simulated environmental conditions. For example, the rate of bioerosion of a material in the eye may be measured by placing a small weighed sample of the material in a 0.9% by weight sodium chloride solution (simulated tear fluids) at body temperature (37°C), agitating for a timed interval, renewing the sodium chloride solution if material solubility considerations make it necessary, and then weighing the sample to determine the weight loss and hence the rate of erosion.

As previously discussed, devices of this invention are designed to dispense a metered amount of drug from the reservoir to the patient over a prolonged period of time, primarily through diffusion or erosion control drug release transfer mechanisms. Moreover, as heretofore indicated, in order to design these devices, it is necessary to correlate drug dosage with permeability characeristics and erosion rates. Methods of determining the rate of passage of drugs by diffusion through drug permeable polymeric material which can readily be adapted to the materials employed in this invention are exemplified in: Dziuk, P. J. and Cook, B., *Passage of Steroids Through Silicone Rubbers*, Endocrinology, 78:208, 1966; U.S. Pat. No. 3,279,996; Folkman and Edmonds, *Circulation Research*, 10:632, 1962, Folkman and Long, *J. Surg. Res.*, 43:139, 1964; Powers, J., *Parasitology*, 51:53 (April 1965), No. 2 Section 2; and copending application Ser. No. 42,786 filed June 2, 1970 now U.S. Pat. No. 3,854,480, of Alejandro Zaffaroni. This application is incorporated herein by reference.

Overall rates of drug release by erosion control mechanism or by combinations of both erosion control and diffusion control mechanisms can be determined directly by placing drug-containing devices under simulated environment conditions and periodically measuring the amount of drug released.

For a more complete understanding of the nature of this invention, reference should be made to the following examples which are given merely as further illustrations of the invention, and are not to be construed in a limiting sense. All parts are given by weight, unless stated to the contrary.

EXAMPLE 1

A bioerodible ocular insert employing a polyvalent metal ion cross-linked polyelectrolyte and containing hydrocortisone is prepared in the following manner:

A. Preparation of zinc alginate -
1. Seven grams of sodium alginate (Keltone, Kelco Co., KT-9529-21) is dissolved in 350 ml of distilled water by means of efficient stirring, to yield a slightly viscous solution.
2. In a separate preparation, 10 grams of zinc chloride is dissolved in 600 ml of distilled water and the pH is adjusted to 3 by drop-wise addition of concentrated hydrochloric acid.
3. The zinc chloride is transferred into a gallon-size Waring blender and to this solution is added in small proportions the sodium alginate solution under moderate agitation. After the addition is complete, the mixture is vigorously stirred for 10–15 minutes, transferred to a glass container and allowed to stand overnight.
4. The precipitate is then transferred to a large size chromatographic column and washed continuously with distilled water to a negative silver chloride test (or to the same conductivity reading as distilled water). The aqueous suspension of the sodium chloride-free zinc alginate is isolated by lyophilization and vacuum-dried at 40°C overnight.

B. Preparation of hydrocortisone ocular insert -
1. The mixture containing 1.5 grams of micronized hydrocortisone in 3.5 grams of glycerine is homogenized by means of a suitable colloid mill or by simple grinding of the mixture with mortar and pestle.
2. The resulting white paste is slowly poured into a Waring blender containing 100 ml of 1.2% ammonium hydroxide solution under vigorous agitation. To this suspension is then added 5 grams of zinc alginate previously prepared, and the vigorous agitation is continued until the complete dissolution of the zinc alginate results; if marked thickening occurs, more ammonia solution can be added.
3. The viscous dispersion of (5) is drawn on a glass plate with a wet thickness of ca. 10 mils. The cast plate is placed in a circulating stream of warm, moisturized air at 40°C, and allowed to dry thoroughly.
4. The resulting film is removed from the plate by stripping, and is punch-cut into desired shape and size. For example, the circular insert device of 6.1 mm diameter and 3 mil thickness contains about 0.45 mg of hydrocortisone. When inserted in a monkey's eye, the resulting insert releases the drug over a two-day period at the termination of which the insert has totally eroded in the eye.

EXAMPLE 2

Plasticized zinc alginate-hydrocortisone acetate and aluminum alginate-hydrocortisone acetate bioerodible ocular inserts are prepared in the following manner:

A. Preparation of sodium alginate-hydrocortisone acetate base -
1. A paste containing 3.2 grams of micronized hydrocortisone acetate and 5.6 mm glycerine is prepared by grinding the mixture with mortar and pestle (or with colloid mill).
2. The paste is transferred into a Waring blender containing 0.03 gram Tween 80 (Atlas Chemical Industries) and 150 ml distilled water. To this fine particle suspension is added 7.5 grams of sodium alginate under vigorous stirring. Alternatively, the Premier-Dispersator (Premier Mill Corp.) may be used for this purpose. If necessary, the whole content may be transferred to a wide-mouth bottle and placed on a variable speed jar mill (Norton Co.) for 12 hours or to complete sodium alginate dissolution.
3. The film is then prepared by casting the mixture on a clean glass plate, and drying it at 40°C for 16 hours. A 125 mil cast of this solution gives about 10 mil thick dry film.

B. Insolubilization -
1. A portion of the plasticized sodium alginate-hydrocortisone acetate film is dipped into 5.5% zinc chloride solution (pH adjusted to 4.5) for 5 hours. The film is then washed twice by immersion in a stirred 50% glycerine bath or until the final washing gives a negative silver chloride test. The film is then air dried at room temperature, and punch-cut into circular discs 6 mm in diameter.

2. An aluminum alginate-hydrocortisone acetate film can also be prepared from the plasticized sodium alginate film by a method analogous to that of zinc alginate film described above using 10% alum (KAl(SO$_4$)$_2$) solution (pH 3.1).

When inserted in the sac of a human eye, the above prepared devices release the drug at a controlled rate. The inserts completely bioerode in the eye at the termination of the therapeutic program. Table I, which follows, characterizes the devices prepared.

TABLE I

CHARACTERISTICS OF HYDROCORTISONE ACETATE CONTAINING METAL-ALGINATE COMPLEXES

| | Zn-Alginate Hydrocortisone Acetate | Al-Alginate Hydrocortisone Acetate |
|---|---|---|
| 1. Hydrocortisone acetate content (H.C.Ac./Alg.) | 30/70 | 30/70 |
| 2. Cross-linking conditions | 5.5% ZnCl$_2$ pH 4.5 5 hrs. | 10% Alum pH 3.1 5 hrs. |
| 3. Tackiness | non-tack | non-tack |
| 4. Color, appearance, etc. | white, smooth | white, smooth |
| 5. Cohesiveness (or intactness on swelling, after 3–4 hrs.) | fair | good |
| 6. Time to erosion (days) | 6 days | >10 days |
| 7. Hydrocortisone acetate release µg/hr | 7 | 1.5 |

EXAMPLE 3

Five polyvalent metal ion cross-linked polyelectrolytes (zinc alginates) having varying ratios of polyelectrolyte to polyvalent ion are prepared and tested as follows:

A. The apparatus, materials and preparative technique described in Part A of Example 1 are used. The amount of zinc chloride employed is varied as follows:

| Preparation Number | Equivalents Alginate / Equivalents Zn II |
|---|---|
| 2 | 1 |
| 3 | 1.5 |
| 4 | 2 |
| 5 | 2.5 |
| 6 | 3 |

B. Preparation of films -

Four-gram portions of the products of part A are each added to 100 ml of 1.2% ammonium hydroxide solution and vigorously stirred to yield viscous solutions. These solutions are drawn on glass plates with wet thickness of about 60 mil and the cast plates thoroughly dried at 40°C in a circulating stream of moist air. This passage of moist air removes the added ammonium hydroxide as well.

C. Testing of films -

1. Erosion Rates.

Seven to 11 mg samples of the resulting films are shaken in 10 cc of 0.9% NaCl solution (saline) at 37°C. Fresh saline is substituted every 30 minutes. The erosion of the samples is monitored and it is observed that the rate of erosion of the samples is related to the ratio of polyelectrolyte to metal ion. Preparation 6, having the least metal ion cross-linking, is the fastest eroding, dissolving in less than 1 hour. Preparations 5 and 4 require from 1 to 2 hours to dissolve. Preparations 3 and 2 require about 5 and 10 hours, respectively, to dissolve.

The erosion rate study is repeated with one change. Instead of saline, deionized water is employed as the erosion environment. After 60 hours, little or no erosion is noted with any of the films, indicating, by comparison with the erosion observed with saline, that the rate controlling mechanism for bioerosion is the gradual displacement of the cross-linking polyvalent metal ions with non-cross-linking monovalent ions of the saline.

2. Liquid Uptake.

Samples of the product denoted Preparation Number 2 (1 equivalent of alginate for each equivalent of zinc) and Preparation Number 3 (1.5 equivalent of alginate for each equivalent of zinc) weighing 0.2052 gram and 0.2901 gram, respectively, are each placed in 100 ml of saline at room temperatures. After one hour, the samples are removed, liquid adhering to the surface is removed, and the samples are weighed. The sample of Preparation 2, the more heavily cross-linked material, has absorbed 40% of its original weight of saline. The sample of Preparation 3, being less tightly cross-linked, has absorbed 111% of its original weight of saline.

Comparison of the liquid uptakes of the two samples shows that the sample of the less thoroughly cross-linked material has achieved a structure having more liquid-filled pores through which drug might more easily and more rapidly diffuse, while the more thoroughly cross-linked material would give a slower rate of drug diffusion.

EXAMPLE 4

A. Zinc II cross-linked alginate containing one equivalent of zinc per equivalent of alginate is prepared in accord with the procedure described in part A of Example 1. 4.15 grams of this cross-linked alginate is dissolved with vigorous stirring in 4.67 ml of 28% NH$_4$OH and 95 ml of deionized water. Separately, a slurry of 0.32 gm of hydrocortisone acetate (Cal Biochem - Lot 100298) is slurried in a minimum amount of water. The slurry is added to the alginate solution and vigorously agitated for 5 to 10 minutes to yield a viscous dispersion which is cast in a film on glass. The film is air dried, subjected to steam treatment to remove residual ammonia, and finally oven dried for 5 minutes at 80°C. Based on the initial weight of dry zinc II cross-linked polyelectrolyte, this product contains about 8% by weight hydrocortisone acetate.

B. This preparation is repeated, varying the amount of drug added, to prepare a film containing 29% of hydrocortisone.

C. Samples of the films of part A and part B are placed in 0.9% saline to determine water uptake. When equilibrium water uptake is reached, the film of part A absorbs 103% of its initial weight of saline, while the film of part B absorbs 95% of its initial weight of saline. Samples of similar film containing no hydrocortisone shows water uptakes of 95–100% of their initial weight. These essentially identical water uptakes indicate that porosity of these films is constant when cross-linking is constant and is essentially independent of drug loading. With constant porosity it would be expected that these materials would have similar rates of drug release by diffusion, irrespective of drug loadings. Six mm diameter discs are punch-cut from a 30 mil thickness film of the material produced in part A (8% drug) and of a 60 mil thickness film of the material produced in part B (29% drug). These discs are inserted in rabbits' eyes, and sequentially removed and weighed to determine erosion rates. The 30 mil film completely erodes in less than 30 hours, while the 60 mil film requires about 40 hours to erode. The devices are compatible with rabbit eyes, causing no untoward irritation.

EXAMPLE 5

Bioerodible ocular inserts are prepared from other representative anionic polyelectrolytes:

A. Preparation of polyelectrolyte drug bases -
1. Pectin.

A solution containing 6 grams (12%) of pectin (Matheson Coleman and Bell Low methoxy grade citrus pectin) and 12% of glycerin in deionized water is prepared in a Waring blender. In a second Waring blender, 1.5 grams of micronized hydrocortisone in 3.5 grams of glycerine is thoroughly homogenized. With vigorous stirring, the contents of the two blenders are combined. An 80 mil wet thickness film is prepared by casting the resulting mixture on a glass plate. The film is air dried at room temperature and then dried at a pressure of less than 1 mm and 40°C for 6 hours to give a 8–10 mil thick dry film.

2. Pectin - Alginate Mixture.

The preparation described in subsection (1) of this part of this Example is repeated with the following changes. Instead of 6 grams of pectin, 3 grams of pectin and 3 grams of sodium alginate are employed; and the amount of hydrocortisone is raised from 1.5 grams to 2.6 grams.

3. Carboxymethyl Cellulose.

The preparation described in subsection (1) of this part of this Example is repeated with the following changes. Instead of 6 grams of pectin, 6 grams of sodium carboxymethyl cellulose powder (Hercules 7 MF Grade) is employed; and the glycerine plasticizer is omitted and replaced with equivalent volume of deionized water.

4. Agar.

minutes in grams of agar (Schwartz-Mann Lot No. W 3435) is suspended in 100 ml of deionized water and heated for 12 minutes in a pressure cooker to yield a clear solution. A paste of 4.28 grams of hydrocortisone acetate and 7.5 grams of glycerine is prepared and added to 20 ml of deionized water. At about 100°C, the paste and solution are combined and stirred to give a homogeneous mixture. A film is prepared from this mixture and dried in accord with subsection (1) of this part of this Example.

B. Insolubilization -

Portions of the four films prepared in part A are insolubilized by being dipped into polyvalent metal ion containing solutions, washed to remove monovalent cations, air dried, and punch-cut into samples for testing. The following polyvalent metal ion polyelectrolyte combinations are made:

1. Pectin Films
   a. With Zn II - The pectin film is dipped in a 40% zinc chloride solution (pH 4.5) for 5 hours.
   b. With Al III - The pectin film is dipped in a 40% aluminum chloride solution (pH 1.55) for 5 hours.
   c. With Ba II - The pectin film is dipped in a 9.77% barium chloride solution (pH 5.8) for 5 hours.
   d. With Ca II - The Pectin film is dipped in a 5.88% calcium chloride solution (pH 6.1) for 5 hours.
2. Pectin-alginate
   a. With Zn II - The pectin-alginate film is dipped in a 40% zinc chloride solution (pH 4.5) for 12 hours.
   b. With Al III - The pectin-alginate film is dipped in a 10% aluminum chloride solution (pH 3.1) for 12 hours.
3. Carboxymethyl Cellulose
   a. With Zn II - The carboxymethyl cellulose film is dipped in a 40% zinc chloride solution (pH 4.5) for 5 hours.
   b. With Al III - The film is dipped in a 4% aluminum chloride solution (pH 3.3) for 5 hours.
4. Agar
   a. With Zn II - The agar film is dipped in a 51.5% zinc chloride solution (pH 4.8) for 12 hours.
   b. With Al III - The agar film is dipped in a 4% aluminum chloride solution (pH 3.3) for 12 hours.
   c. With Ba II - The agar film is dipped in a 9.77% barium chloride solution (pH 5.8) for 12 hours.
   d. With Ca II - The agar film is dipped in a 5.88% calcium chloride solution (pH 6.1) for 12 hours.
5. Alginate Portions of a sodium alginate film containing 30% hydrocortisone acetate, as prepared in Example 2, are dipped into 30.9% barium chloride solution (pH 4.5) for 12 hours, a 30.0% calcium chloride solution (pH 6.7) for 12 hours, a 20% ferric chloride solution (pH 4) for 12 hours, and a 20% cadmium nitrate solution (pH 4) for 12 hours.

If cut into suitable shapes and inserted into the sac of an eye, the above prepared metal ion cross-linked materials would release the drug at a controlled rate and completely bioerode in the environment of the sac of the eye at the termination of the therapeutic program. Table II, which follows, characterizes the materials prepared.

TABLE II

Characteristics of hydrocortisone acetate containing polyvalent metal ion linked polyelectrolytes.

| CHARACTERISTIC | PECTIN | | | |
| --- | --- | --- | --- | --- |
|  | Zn II | Al III | Ba II | Ca II |
| 1. Hydrocortisone acetate content (H.C. Ac/Alg.) | 20/80 | 20/80 | 20/80 | 20/80 |
| 2. Tackiness | non-tack. | non-tack. | non-tack. | non-tack. |
| 3. Flexibility | soft, flex. | brittle | flex. | flex. |
| 4. Color, Appearance, etc. | white, smooth | white, smooth | white, smooth | white, smooth |
| 5. Cohesiveness (or intactness) on swelling (after 3–4 hrs) | poor | fair-good | fair-good | fair |

TABLE II-continued

Characteristics of hydrocortisone acetate containing polyvalent metal ion linked polyelectrolytes.

| | | | | | |
|---|---|---|---|---|---|
| 6. | Time to Erosion (hr) (in 0.9% — NaCl) for 9–12 mil Film | 1 | 110+ | 60+ | 0.5–1 |
| 7. | Hydrocortisone acetate release $\mu$g/hr. | 100+ | 4 | 7 | 100+ |

| CHARACTERISTIC | CARBOXYMETHYL CELLULOSE | |
|---|---|---|
| | Zn II | Al III |
| 1. Hydrocortisone acetate content (H.C. Ac/Alg.) | 30/70 | 30/70 |
| 2. Tackiness | non-tack | non-tack. |
| 3. Flexibility | sl. flex. | sl. flex. |
| 4. Color, Appearance, etc. | white, rough | white, rough |
| 5. Cohesiveness (or intactness) on swelling (after 3–4 hrs) | poor | poor |
| 6. Time to Erosion (hr) (in 0.9% — NaCl) for 9–12 mil Film | — | >300 |
| 7. Hydrocortisone acetate release $\mu$g/hr. | — | 7 |

| CHARACTERISTIC | PECTIN-ALGINATE | |
|---|---|---|
| | Zn II | Al III |
| 1. Hydrocortisone acetate content (H.C. Ac/Alg.) | 30/70 | 30/70 |
| 2. Tackiness | non-tack. | non-tack. |
| 3. Flexibility | sl. flex. | brittle |
| 4. Color, Appearance, etc. | white, smooth | white, smooth |
| 5. Cohesiveness (or intactness) on swelling (after 3–4 hrs) | poor | fair |
| 6. Time to Erosion (hr) (in 0.9% — NaCl) for 9–12 mil Film | 24 | 24 |
| 7. Hydrocortisone acetate release $\mu$g/hr. | 10 | 4 |

| CHARACTERISTIC | AGAR | | | |
|---|---|---|---|---|
| | Zn II | Al III | Ba II | Ca II |
| 1. Hydrocortisone acetate content (H.C. Ac/Alg.) | 30/70 | 30/70 | 30/70 | 30/70 |
| 2. Tackiness | sl. tack. | non-tack. | non-tack | sl. tack |
| 3. Flexibility | brittle | brittle | brittle | brittle |
| 4. Color, Appearance, etc. | sl. tan, smooth | sl. tan, smooth | sl. tan, smooth | sl. tan, smooth |
| 5. Cohesiveness (or intactness) on swelling (after 3–4 hrs) | fair-poor | fair-poor | fair-poor | fair-poor |
| 6. Time to Erosion (hr) (in 0.9% — NaCl) for 9–12 mil Film | 100+ | 180+ | 180+ | 100+ |
| 7. Hydrocortisone acetate release $\mu$g/hr. | 6–8 | 6–8 | 6–8 | 5 |

| CHARACTERISTIC | ALGINATE | | | |
|---|---|---|---|---|
| | Ba II | Ca II | Fe III | Cd II |
| 1. Hydrocortisone acetate content (H.C. Ac/Alg.) | 30/70 | 30/70 | 30/70 | 30/70 |
| 2. Tackiness | non-tack. | non-tack. | non-tack. | non-tack. |
| 3 Flexibility | flex. | flex. | sl. flex. | sl. flex. |
| 4. Color, Appearance, etc. | white, smooth | white, smooth | brown, smooth | sl. yel. smooth |
| 5. Cohesiveness (or intactness) on swelling (after 3–4 hrs) | good-fair | fair | fair | fair |

TABLE II-continued

Characteristics of hydrocortisone acetate containing polyvalent metal ion linked polyelectrolytes.

| | | | | |
|---|---|---|---|---|
| 6. Time to Erosion (hr) (in 0.9% — NaCl) for 9–12 mil Film | 50+ | 20+ | 30+ | 30+ |
| 7. Hydrocortisone acetate release μg/hr. | 4 | 6 | 5 | 4–6 |

EXAMPLE 6

Five hundred grams of chloramphenicol of a particle size of 50 microns is encapsulated with polylactic acid polymer of molecular weight 50,000, according to the following procedure. Two hundred and fifty grams of the polylactic acid is dissolved into 2 liters of chloroform. The chloramphenicol particles are coated by polylactic acid using Wurster air suspension technique. The coat thickness is determined to be 30 microns thick.

Separately, in a Waring blender, 10 grams of sodium alginate is vigorously stirred with 300 ml of deionized water to yield a slightly viscous solution.

Stirring is stopped and 3 grams of the chloramphenicol microcrystals are thoroughly dispersed in the sodium alginate solution. The final mixture is then cast on a clean glass plate leveled with a doctor's blade to a thickness of 80 mils, and dried for 24 hours in a stream of circulating 35°C air. The resulting film is removed from the glass plate by stripping, and immersed in a 6% by weight zinc chloride solution (ph 5.0) for 12 hours. The film is then repeatedly washed until a washing gives a negative chloride test. The film is then air dried at room temperature and punch-cut into elliptically shaped ovals 8 mm in major axis and 5 mm in minor axis. When these ovals are placed in the sacs of eyes, they release chloramphenicol for a prolonged period of time at a rate controlled by the polylactic acid microencapsulation polymer. The metal ion linked polyelectrolyte which functions as a matrix for the microcapsules, completely bioerodes in the environment of the eye at the termination of the therapeutic program.

EXAMPLE 7

Ten grams of sodium alginate, 20 grams of glycerine and 180 grams of deionized water are combined with vigorous stirring to give a clear viscous solution. To this solution is added 0.5 grams of micronized progesterone crystals and the mixture is vigorously agitated to achieve a uniform suspension. The suspension is then cast on a glass plate and drawn to a wet thickness of 150 mils. The cast plate is placed in a circulating stream of 40°C air and allowed to dry.

The resulting film is stripped from the plate and immersed in a 10% solution of aluminum chloride at pH 3.1 for 12 hours. The film is then washed in a 10% by weight glycerine solution until a negative chloride test results. The film is then removed, dried in air and cut into 40 mg pieces. These pieces are then implanted in female Holtzman rats where they produce an estrogenic response lasting for about two weeks.

EXAMPLE 8

Ocular inserts of the type set forth in FIGS. 4 and 5 include devices comprising the following combinations of drug, inner reservoir and outer rate controlling membrane:

1. An inner reservoir of hydrocortisone acetate dispersed in a poly(vinyl alcohol) matrix with the outer rate controlling membrane material being an aluminum ion cross-linked plasticized pectin.
2. An inner reservoir of hydrocortisone acetate surrounded by a membrane of zinc II cross-linked plasticized alginate.

What is claimed is:

1. A delivery device for the sustained administration of a predetermined dosage of an ophthalmic drug to the eye of a mammalian patient comprising (1) an inner reservoir comprised of a biodegradable material that degrades to innocuous products in response to the biological ocular environment of the patient, said reservoir containing an ophthalmic drug formulation confined therein, and (2) an outer membrane surrounding the inner reservoir, the membrane permeable to the passage of ophthalmic drug, but at a lower rate than through the inner reservoir, the membrane formed from drug release rate controlling bioerodible material consisting of a polyvalent metal ion cross-linked anionic polyelectrolyte, said ion a member selected from the group consisting of aluminum, barium, cadmium, calcium, copper, iron, zinc and mixtures thereof, said polyelectrolyte a member selected from the group consisting of cellulose, hemicellulose, starch, polystyrene sulfonic acid, polyvinyl sulfonic acid, polyvinyl methylol sulfonic acid, polyacrylic acid, polymethacrylic acid, acrylic copolymers, methacrylic copolymers, polyvinyl alcohol, polyvinyl chloride, glycans and polysaccharides, which outer membrane bioerodes in the eye of the patient in response to the biological environment therein by a process of polyvalent metal ion displacement by noncross-linking ions present in the eye, and wherein when in the ocular environment the membrane continuously meters the flow of a therapeutically effective amount of ophthalmic drug from the reservoir to the eye of the patient at a controlled and continuous rate over a prolonged period of time.

2. The delivery device according to claim 1 wherein the inner reservoir is formed of poly(lactic acid) containing an ophthalmic drug, and the outer membrane is formed of zinc chloride cross-linked alginate.

3. A device for administering an ophthalmic drug to the eye according to claim 1 wherein the drug is a member selected from the group consisting of tetracycline, chlortetracycline, bacitracin, neomycin, polymyxin, gramicidin, oxytetracycline, chloramphenicol, gentamycin, and erthromycin.

4. A device for administering an ophthalmic drug to the eye according to claim 1 wherein the drug is a member selected from the group consisting of hydrocortisone, hydrocortisone acetate, dexamethasone, dexamethasone 21-phosphate, fluocinolone, medrysone, prednisolone, methylprednisolone, predisolone 21-phosphate, prednisolone acetate, fluoromethalone, betamethasone, and triamcinolone.

5. A device for administering an ophthalmic drug to the eye according to claim 1 wherein the drug is a member selected from the group consisting of idoxuridine, pilocarpine, phospholine iodide, demecarium bromide, cyclopentolate, hematropine, scopolamine, epinephrine and eserine salicylate.

6. A bioerodible delivery device for the sustained administration of a predetermined dosage of ophthalmic drug to the eye of a mammalian patient consisting of a matrix of polyvalent cation cross-linked anionic polyelectrolyte material that bioerodes in the biological ocular environment by displacement of the cation by a noncross-linking ion to form a non-toxic product, said material having distributed throughout a plurality of microporous reservoirs with each of the reservoirs consisting of an ophthalmic drug formulation confined within the rate controlling material, the reservoir characterized by being selected from a group consisting of (1) a microcapsule of an initial size and configuration capable of being eliminated from the ocular cavity through the punctum with tear fluid and formed of a material that degrades to innocuous products in response to the biological environment, and (2) a microcapsule of biodegradable material that degrades to innocuous products in the eye in response to the ocular environment; the matrix material being permeable to the passage of ophthalmic drug at a higher rate than through the drug release rate controlling material with the latter material metering a therapeutically effective amount of ophthalmic drug from the reservoir to the eye of the patient at a controlled and continuous rate over a prolonged period of time.

7. The delivery device according to claim 6 wherein the microcapsules are formed of poly(lactic acid) containing an ophthalmic drug and the matrix is formed of zinc chloride cross-linked alginate.

8. A device for administering an ophthalmic drug to the eye according to claim 6 wherein the drug is a member selected from the group consisting of antibiotic, antibacterial, antiviral, antiallergenic, anti-inflammatory, miotic, antichlolinesterase, decongestant and sympathomimetic drugs.

9. A device for administering an ophthalmic drug to the eye according to claim 6 wherein the drug is a member selected from the group consisting of idoxuridine, pilocarpine, phospholine iodide, demecarium bromide, cyclopentolate, hematropine, scopolamine, epinephrine, and eserine salicylate.

* * * * *